US012743151B2

(12) United States Patent
Basile, Jr.

(10) Patent No.: US 12,743,151 B2
(45) Date of Patent: *Sep. 22, 2026

(54) VIRTUAL REALITY SYSTEM WITH POSTURE CONTROL

(71) Applicant: Andrew R. Basile, Jr., Troy, MI (US)

(72) Inventor: Andrew R. Basile, Jr., Troy, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/176,219

(22) Filed: Apr. 11, 2025

(65) Prior Publication Data

US 2026/0003423 A1 Jan. 1, 2026

Related U.S. Application Data

(63) Continuation of application No. 17/404,833, filed on Aug. 17, 2021, now Pat. No. 12,277,258, which is a continuation of application No. 15/349,153, filed on Nov. 11, 2016, now Pat. No. 11,099,631.

(60) Provisional application No. 62/254,868, filed on Nov. 13, 2015.

(51) Int. Cl.

| | |
|---|---|
| ***G06F 3/01*** | (2006.01) |
| ***A61B 5/00*** | (2006.01) |
| ***G02B 27/01*** | (2006.01) |
| ***G06F 3/0346*** | (2013.01) |

(52) U.S. Cl.

CPC ............ *G06F 3/011* (2013.01); *A61B 5/0077* (2013.01); *A61B 5/4561* (2013.01); *G02B 27/017* (2013.01); *G06F 3/017* (2013.01); *G06F 3/0346* (2013.01)

(58) Field of Classification Search

None

See application file for complete search history.

(56) References Cited

U.S. PATENT DOCUMENTS

| | | | |
|---|---|---|---|
| 4,871,998 | A | 10/1989 | Chaillou |
| 5,199,940 | A | 4/1993 | Morris et al. |
| 7,095,424 | B2 | 8/2006 | Satoh et al. |
| 7,308,332 | B2 | 12/2007 | Okada et al. |
| 7,433,753 | B2 | 10/2008 | Okada et al. |
| 7,809,159 | B2 | 10/2010 | Ishiyama |
| 8,011,229 | B2 | 9/2011 | Lieberman et al. |
| 8,135,209 | B2 | 3/2012 | Ikeda |
| 8,150,531 | B2 | 4/2012 | Skelton |
| 8,200,340 | B2 | 6/2012 | Skelton et al. |
| 8,249,718 | B2 | 8/2012 | Skelton et al. |
| 8,315,710 | B2 | 11/2012 | Skelton et al. |
| 8,326,420 | B2 | 12/2012 | Skelton et al. |
| 8,332,041 | B2 | 12/2012 | Skelton et al. |
| 8,419,594 | B2 | 4/2013 | Motoyashiki |
| 8,447,411 | B2 | 5/2013 | Skelton et al. |
| 8,504,150 | B2 | 8/2013 | Skelton |
| 8,515,549 | B2 | 8/2013 | Panken et al. |
| 8,583,252 | B2 | 11/2013 | Skelton et al. |
| 8,644,945 | B2 | 2/2014 | Skelton et al. |
| 8,663,119 | B2 | 3/2014 | Izumi et al. |
| 8,886,302 | B2 | 11/2014 | Skelton et al. |

(Continued)

*Primary Examiner* — Ifedayo B Iluyomade

(74) *Attorney, Agent, or Firm* — Young Basile Hanlon & MacFarlane, P.C.

(57) ABSTRACT

A method includes rendering a first field of view of a scene in accordance with a determination that the posture of the user corresponds to good posture and rendering a second field of view of a scene in accordance with a determination that the posture of the user corresponds to bad posture.

20 Claims, 6 Drawing Sheets

(56) References Cited

U.S. PATENT DOCUMENTS

| | | | |
|---|---|---|---|
| 8,958,885 B2 | 2/2015 | Panken et al. | |
| 9,050,471 B2 | 6/2015 | Skelton et al. | |
| 9,072,461 B2 | 7/2015 | Menegon et al. | |
| 9,129,077 B2 | 9/2015 | Raschke | |
| 9,177,457 B2 | 11/2015 | Shin et al. | |
| 9,272,091 B2 | 3/2016 | Skelton et al. | |
| 9,275,276 B2 | 3/2016 | Kawaguchi | |
| 9,327,070 B2 | 5/2016 | Skelton et al. | |
| 9,398,972 B2 | 7/2016 | Yip et al. | |
| 9,420,963 B2 | 8/2016 | Kim et al. | |
| 9,436,871 B2 | 9/2016 | Liu et al. | |
| 9,500,885 B2 | 11/2016 | Kubitza et al. | |
| 9,545,518 B2 | 1/2017 | Panken et al. | |
| 11,099,631 B2 * | 8/2021 | Basile, Jr. | G06F 3/011 |
| 2013/0278497 A1 | 10/2013 | Takagi et al. | |
| 2014/0028458 A1 * | 1/2014 | Shin | A61B 5/4561 340/573.7 |
| 2016/0026242 A1 | 1/2016 | Burns et al. | |
| 2016/0027215 A1 | 1/2016 | Burns et al. | |
| 2016/0035208 A1 | 2/2016 | Shin et al. | |

* cited by examiner

VIRTUAL REALITY SYSTEM WITH POSTURE CONTROL

CROSS-REFERENCE TO RELATED APPLICATIONS

This application is a continuation of U.S. patent application Ser. No. 17/404,833, filed on Aug. 17, 2021, which is a continuation of U.S. patent application Ser. No. 15/349,153, filed on Nov. 11, 2016, now U.S. Pat. No. 11,099,631, which claims the benefit of U.S. Provisional Application No. 62/254,868, filed on Nov. 13, 2015. The contents of the foregoing applications are incorporated by reference herein in their entireties for all purposes.

TECHNICAL FIELD

This disclosure relates to virtual reality systems using computing devices adapted to control user's posture while using the virtual reality system.

BACKGROUND

Virtual reality systems can include computing devices adapted to permit a user to experience a virtual reality, where virtual reality can be defined as a data set, stored at a computing device, for example, that describes at least a portion of one or more virtual reality worlds. These portions of virtual reality worlds are described in sufficient detail to permit rendering a plurality of fields of view that present to the user scenes from the virtual physical worlds. These fields of view can include renderings of scenery, objects, buildings, and people combined to form a simulation of a virtual world. The virtual world can be a replication of a real place, for example a virtual tour of a famous landmark, or an imaginary or normally inaccessible place such as space. Virtual reality systems can permit a user to navigate through a virtual world and interact with imaginary or simulations of real objects, people, and environments by changing fields of view presented to the user in an appropriate fashion.

SUMMARY

This disclosure includes aspects of systems, methods, and apparatuses for outputting fields of view of a virtual reality system according to postures of a user of the virtual reality system. The virtual reality system outputs a field of view to a display. A sensor of the virtual reality system then detects a posture of the user. The virtual reality system alters the field of view in response to the detection of the user's posture.

Another aspect of a disclosed implementation is an apparatus. The apparatus includes a memory and a processor operative to execute instructions stored in the memory to select, render, and display a field of view on the virtual reality headset. The apparatus detects, using a sensor operative to detect one or more bad postures of the user, one or more bad postures. When the one or more bad postures are detected, the virtual reality headset indicates to the user that the one or more bad postures are detected by selecting, rendering, and displaying an altered field of view on the virtual reality headset. When the one or more postures are not detected, the virtual reality headset indicates to the user that the one or more bad postures are not detected by selecting, rendering, and displaying the field of view on the virtual reality headset.

An aspect of the disclosure is a method. The method includes obtaining a posture signal indicative of a posture of a user of a virtual reality display system. The method also includes outputting a field of view of a virtual reality scene to the virtual reality display system. The field of view is a motion tracked field of view when the posture signal corresponds to good posture. The field of view is a moved field of view when the posture signal corresponds to bad posture.

In some implementations of the method, the method includes obtaining a motion signal, wherein the motion tracked field of view is determined based on the motion signal. In some implementations of the method, the moved field of view differs from the motion tracked field of view. In some implementations of the method, the moved field of view ignores the motion signal. In some implementations of the method, the motion signal represents a location and attitude of the virtual reality display system. In some implementations of the method, the motion signal is obtained using one or more accelerometers. In some implementations of the method, the posture signal is determined using at least one of a video camera or a three-dimensional sensor. In some implementations of the method, the virtual reality display system is worn by the user on a head of the user.

These and other aspects are described in additional detail below.

BRIEF DESCRIPTION OF THE DRAWINGS

This disclosure refers to the accompanying drawings, where like reference numerals refer to like parts throughout the several views and wherein.

DETAILED DESCRIPTION

Figure 1:
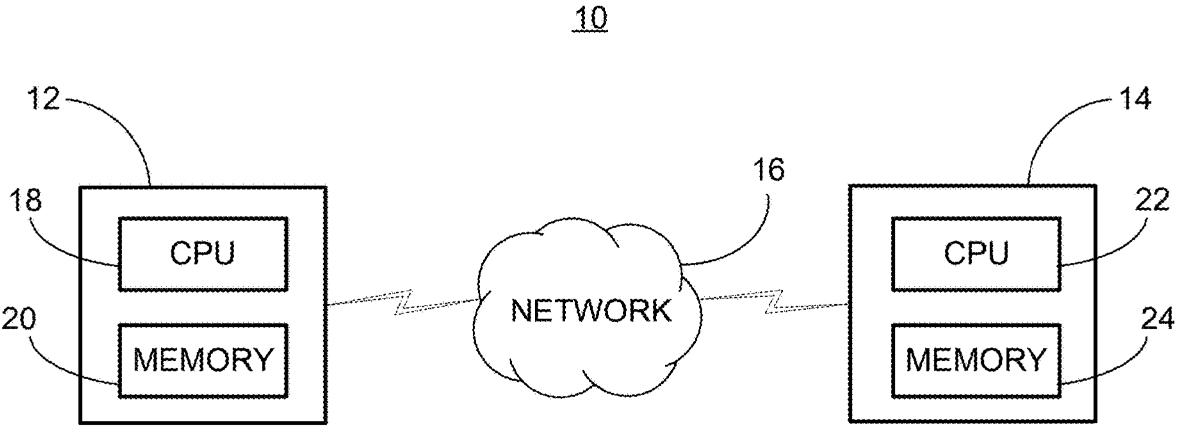
FIG. 1 is a diagram of computing devices and a network in accordance with aspects of disclosed implementations.

Virtual reality (VR) systems can present fields of view to a user via a display to provide the user with the perception of being in an environment other than reality. A field of view presents to the user scenes from a virtual reality world. Virtual reality systems can use an opaque background for the displayed fields of view or use a transparent background so that the field of view is overlaid on the user's view of the real world. Virtual reality systems can also acquire a video stream of the real world and superimpose objects and people on the video stream representing the real world. These latter two schemes can be called augmented reality. Examples of virtual reality systems include car racing simulators, flight simulators, video games and video conferencing systems. Virtual reality systems can permit a user to simulate driving vehicles, flying airplanes, exploring alien worlds or being at a simulated meeting with participants from different parts of the world without any of the participants leaving home, for example.

The fields of view that comprise the virtual reality world can be arranged to provide the user with the perception of being in a virtual world. The fields of view can change according to the simulated physical dynamics of the world being simulated. For example, in a driving or flying system, the fields of view will change according to the simulated motion of the vehicle or airplane. Fields of view can also be changed by the user interacting with a controller, for example. Many video games are controlled by a handheld controller that includes buttons and switches that can change the point of view of the user in the virtual world and hence the fields of view displayed. The displays of some virtual reality systems include a virtual reality headset, for example. Accelerometers can be used in a virtual reality headset to detect the location and attitude of the headset and thereby control the field of view to track the user's head motions (e.g., obtaining motion data or a motion signal) and arrange the field of view accordingly. Virtual reality systems can include other types of displays such as a stationary screen in front of the user not worn on a headset, multiple stationary screens surrounding the user, screens placed on lenses worn on the user's eyes, or hologram images projected around the user.

None of these three ways to control the field of view selection have the ability to display fields of view to the user that reflect the posture of the user properly. In real life, if a person assumes bad posture, cues in the immediate real-world environment can alert the user that bad posture has been assumed. For example, if a person slouches in a chair, they will see different elements from the environment enter their visual field, like parts of their own body. With a virtual reality system, since the fields of view are at least partially synthetic, they may not include the visual cues normally associated with bad posture. Aspects of disclosed implementations detect bad posture using an external device to observe the user. When bad posture is detected, the virtual reality system can change the field of view to alert the user that bad posture has been detected. When the bad posture is remedied, the virtual reality system can return the field of view to the view before the bad posture was detected.

FIG. 1 is a schematic of a virtual reality system 10 in which aspects of the invention can be implemented. A computing device 12, in one example, can include an internal configuration of hardware including a processor such as a central processing unit (CPU) 18 and a digital data storage exemplified by memory 20. CPU 18 can be a controller for controlling the operations of computing device 12, and may be a microprocessor, digital signal processor, field programmable gate array, discrete circuit elements laid out in a custom application specific integrated circuit (ASIC), or any other digital data processor, for example. CPU 18 can be connected to memory 20 by a memory bus, wires, cables, wireless connection, or any other connection, for example. Memory 20 may be or include read-only memory (ROM), random access memory (RAM), optical storage, magnetic storage such as disk or tape, non-volatile memory cards, cloud storage or any other manner or combination of suitable digital data storage device or devices. Memory 20 can store data and program instructions (e.g., computer interpretable program instructions) that are used by CPU 18. Other suitable implementations of computing device 12 are possible. For example, the processing of computing device 12 can be distributed among multiple devices communicating over multiple networks 16.

In one example, a network 16 can connect computing device 12 and computing device 14 for displaying a virtual reality world. For example, a database can be included in computing device 12 and accessed via applications executing in computing device 14. Network 16 may include any network or networks that are appropriate to the application at hand, such as wired or wireless local or wide area networks, virtual private networks, cellular telephone data networks, or any other wired or wireless configuration of hardware, software, or communication protocol suitable to transfer a video bitstream from computing device 12 to computing device 14 and communicate parameters regarding the network from computing device 14 to computing device 12 in the illustrated example.

Computing device 14 can include CPU 22 and memory 24, which can be similar to components as discussed above in conjunction with the computing device 12. Computing device 14 can be configured to display a web browser, for example. A display connected to computing device 14 can be implemented in various ways, including by a liquid crystal display (LCD), a cathode-ray tube (CRT), organic or non-organic light emitting diode display (LED), plasma display, or any other mechanism to display a machine-readable video signal to a user. Computing device 14 can be configured to display a web page including information from a database included in computing device 12, for example.

Other implementations of virtual reality system 10 are possible. Computing device 12 and computing device 14 can include servers and mobile phones, which can also create, store, forward or display digital information regarding human resource management, for example. Each of these computing devices can have differing capabilities in terms of processing power and memory availability, including devices for creating video such as video cameras and devices for displaying video.

Figure 2:
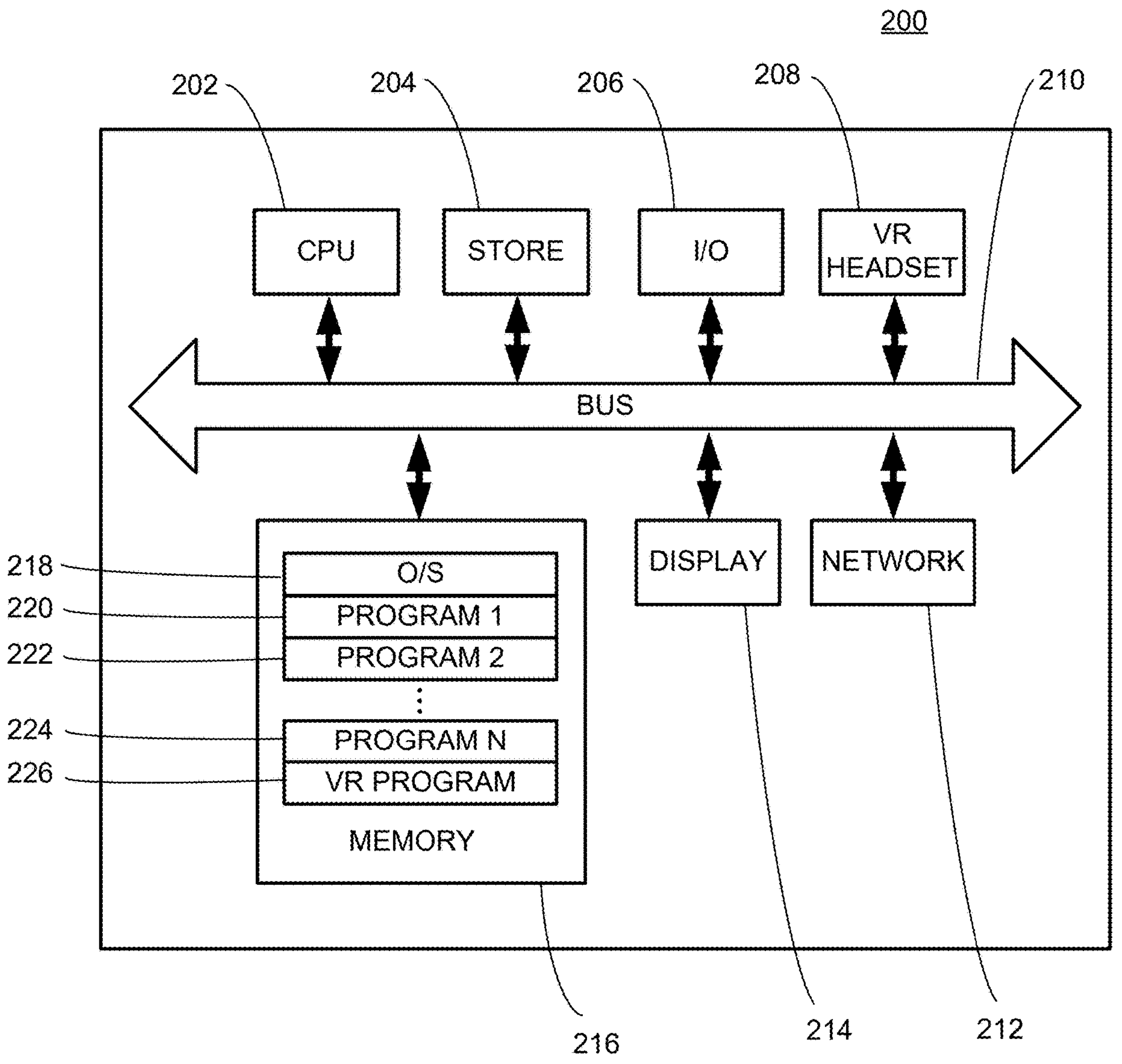
FIG. 2 is a diagram of a computing device in accordance with aspects of disclosed implementations.

FIG. 2 is a diagram of a virtual reality computing device 200. The virtual reality computing device 200 can include a CPU 202 operative to execute instructions read via bus 210 from memory 216. Memory 216 can include software programs including an operating system (O/S) 218 and various software programs including program 1 220, program 2 222 up to program N 224. Memory 216 can include virtual reality software (VR program) 226, which, when executed by CPU 202, can cause the virtual reality computing device 200 to operate as a virtual reality system. The virtual reality computing device 200 can also include a display controller (display) 214 for connecting an output display device such as an LCD screen to the virtual reality computing device 200. In one example, The virtual reality computing device 200 also includes a non-transitory storage 204 (e.g., a non-transitory computer-readable storage device). Programs and data can be stored in the non-transitory storage 204 for retrieval at a later time. The non-transitory storage 204 can include disk drives and other types of rotating memory including CDROM, solid state drives including SD cards, or cloud storage, which can be accessed via network interface (network) 212. The virtual reality computing device 200 can also include input/output adapters 206 (I/O) that can connect input/output devices such as keyboards, trackpads, or game controllers to the virtual reality computing device 200. The input/output adapters can also connect the virtual reality computing device 200 to video cameras or three-dimensional sensors, for example, in accordance with disclosed implementations.

The virtual reality computing device 200 can include a virtual reality headset 208 (VR headset), which can be worn by a user to facilitate experiencing the virtual reality system. The virtual reality computing device 200 can also include a computer, a mobile device, a server, or any combination thereof. The virtual reality headset 208 can constitute a display of the virtual reality system 400, wherein the display outputs data indicative of a field of view according to the user's posture. The virtual reality headset 208 can use video display technology to create displays that effectively cover the user's visual field. When wearing the virtual reality headset 208, a user's entire visual perceptional field can be supplied as successive fields of view by the virtual reality system, thereby producing the effect of viewing scenes from a virtual world. In addition to display capabilities, The virtual reality headset 208 can also be equipped with accelerometers, for example, that can measure the location and attitude of the virtual reality headset 208 and thereby the location and attitude of the user's head.

Figure 3:
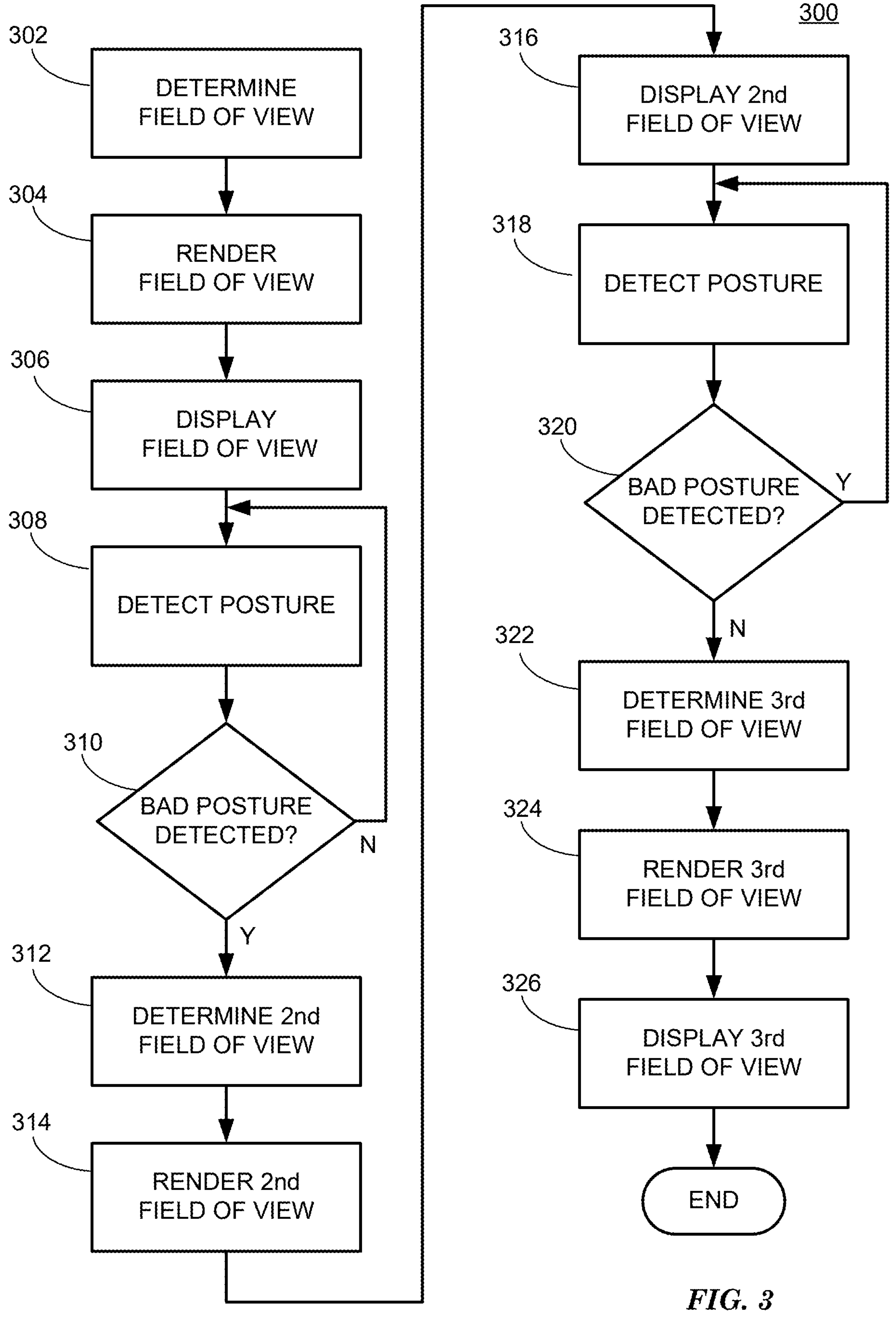
FIG. 3 is a flowchart diagram of a virtual reality posture control system in accordance with aspects of disclosed implementations.

FIG. 3 is a flowchart showing a process 300 for posture control with a virtual reality system in accordance with disclosed implementations. Process 300 can be performed by the virtual reality computing device 200 for example. The flowchart diagram in FIG. 3 shows several steps included in process 300. Process 300 can be accomplished with the steps included herein or with more or fewer steps than included here. For example, steps can be combined or divided to change the number of steps performed. The steps of process 300 can be performed in the order included herein or in different orders and still accomplish the intent of process 300.

Figure 4:
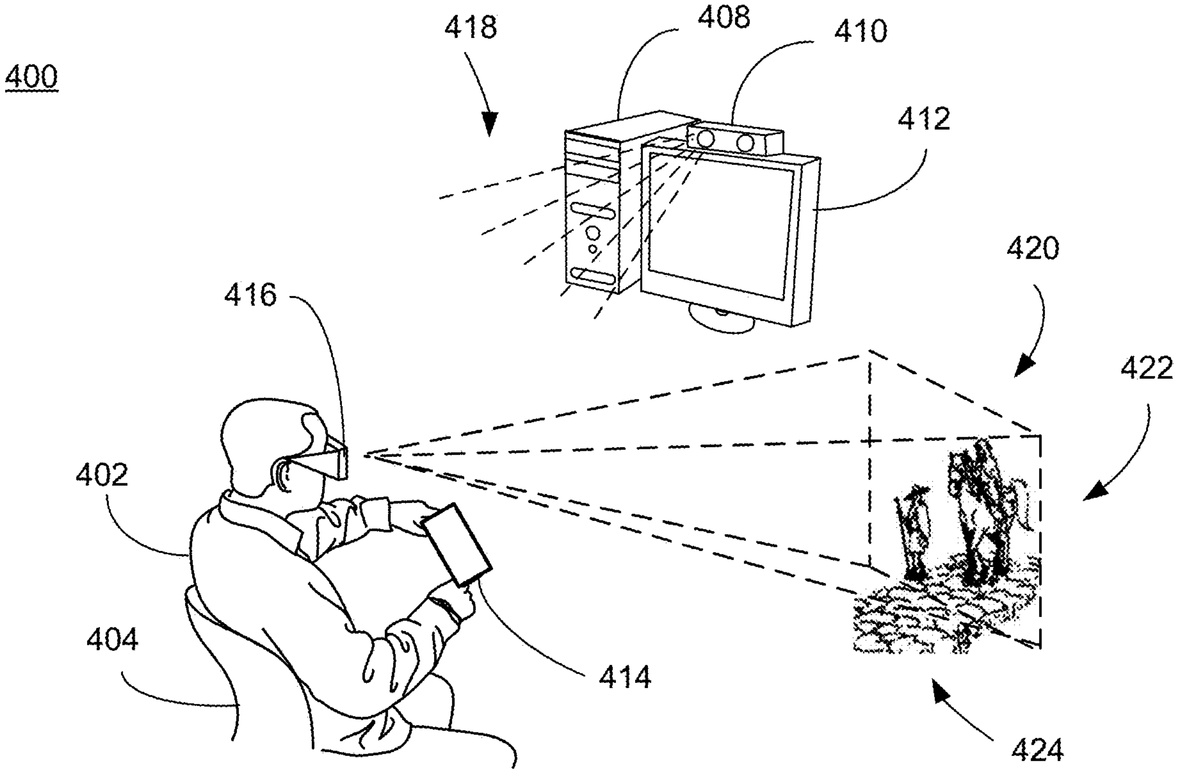
FIG. 4 is a diagram of a user at a virtual reality system in accordance with aspects of disclosed implementations.

Process 300 begins at step 302 by determining a field of view. Determining a field of view can mean creating, destroying, altering, computing, calculating, selecting, storing, retrieving, or any other processing or change related to a field of view in a virtual reality system. A field of view can be defined with reference to FIG. 4. FIG. 4 is a diagram of a virtual reality system 400. Virtual reality system 400 includes a user 402 seated in a chair 404, for example. A virtual reality headset 416 can display to the user a scene 422 based on a virtual world 424. Determining the field of view 420 determines which scene (e.g., the scene 422) from the virtual world 424 is to be rendered and displayed to user 402. In one example, a computing device 408 can output a field of view 420 to a display of the virtual reality system 400. The display could include the virtual reality headset 416.

Returning to FIG. 3, at step 304, a field of view can be rendered for display on the virtual reality headset 416. At step 306 the field of view including a scene 422 can be displayed on the virtual reality headset 416. As discussed above, virtual reality systems can present to the user, via the virtual reality headset 416, one or more fields of view 420 that can permit a user to imagine that they are viewing portions of an unreal or "virtual" reality. Virtual reality system 400 can include a user 402 seated in a chair 404, for example. User 402 can wear the virtual reality headset 416 and hold a controller 414 with which to communicate with the computing device 408 having a display 412. The computing device 408 can determine the location of one or more fields of view 420 with respect to the virtual world 424 and thereby determine scenes such as the scene 422 to display on the virtual reality headset 416 for viewing by user 402. The scene 422 can be a portion of the virtual world 424 that includes many, many possible scenes, for example. By changing the location of field of view 420 with respect to the virtual world 424, virtual reality system 400 can create the experience of moving and looking around in the virtual world 424, for example.

In one example, the field of view 420 is determined by the computing device 408 of the virtual reality system 400 independently of the posture of the user. In this example, user 402 can determine the location of the field of view 420, and therefore which scene (e.g., the scene 422) from the virtual world 424 to display using the virtual reality headset 416, by inputting commands to the computing device 408 via controller 414. The computing device 408 can be implemented on a server, computer, virtual reality headset, mobile device, or any combination thereof. In this case, the location of the field of view 420 with respect to the virtual world 424 is determined by the computing device 408 independently of the location and attitude of the virtual reality headset 416. In such an example, the display, which could include the virtual reality headset 416, outputs data indicative of a field of view independently of the posture of the user when a sensor 410 does not detect a posture of the user. User 402 can cause the VR headset to mimic motions of the head and body that result in "looking around" the virtual world 424 by inputting commands via the controller 414, for example. In any case, the location of the field of view 420 is independent of the position of the virtual reality headset 416.

When the scene 422 displayed using the virtual reality headset 416 is independent of the location and attitude of the virtual reality headset 416, the scene 422 is also independent of user's posture. Therefore, a user 402 can, while engrossed in viewing the virtual world 424 for example, inadvertently assume a bad posture. With no feedback from the user's real world visual field, bad posture can continue and result in deleterious effects to the user 402. Aspects of disclosed implementations detect user's bad posture with a sensor 410 and alert the user 402 of detected bad posture by changing the user's field of view 420. By changing the field of view 420 to mimic changes in a user's real-world field of view when exhibiting bad posture, the physical action to correct the bad posture can be naturally and unobtrusively elicited.

Virtual reality system 400 can include a sensor 410 having a sensor field of view 418. In one example, sensor 410 of the virtual reality system 400 detects a posture of the user. Sensor 410 is operative to detect the position and thereby the posture of user 402 when user 402 is within sensor field of view 418. Sensor 410 can include one or more video cameras, for example, connected to the computing device 408. Software programs executing on the computing device 408 can use machine vision techniques to determine the position of user 402 and thereby user's posture. Sensor 410 can also include one or more three-dimensional sensors, which when connected to the computing device 408, can detect a user's posture. The computing device 408 can include a memory and a processor configured to execute instructions stored in the memory to: transmit data indicative of a field of view 420, receive data indicative of a posture of the user (e.g., obtaining posture data or a posture signal) from a sensor 410 of the virtual reality system 400, and transmit data indicative of an altered field of view 506 according to the posture.

In one example, the posture of the user detected using the sensor 410 is predetermined for the user. A subset of the possible postures that can be detected for a user can be predetermined to be "bad" postures. Thereafter, the sensor 410 can periodically detect the user's posture by acquiring video images of the sensor field of view 418. For example, sensor 410 can detect a user's posture once per second. When the user's detected posture becomes similar to a posture previously determined to be a bad posture, bad posture can be detected by virtual reality system 400, for example.

Returning to FIG. 3, at step 308 a user's posture can be detected as discussed above in relation to FIG. 4. At step 310, process 300 can determine whether the detected posture is a bad posture. If no bad posture is detected, process 300 can return to step 308 to periodically detect user's posture. If bad posture is detected at step 310, process 300 passes to step 312. Step 312 can be described with reference to FIG.

Figure 5:
FIG. 5 is a diagram of a user at a virtual reality system in accordance with aspects of disclosed implementations.
Figure 5:
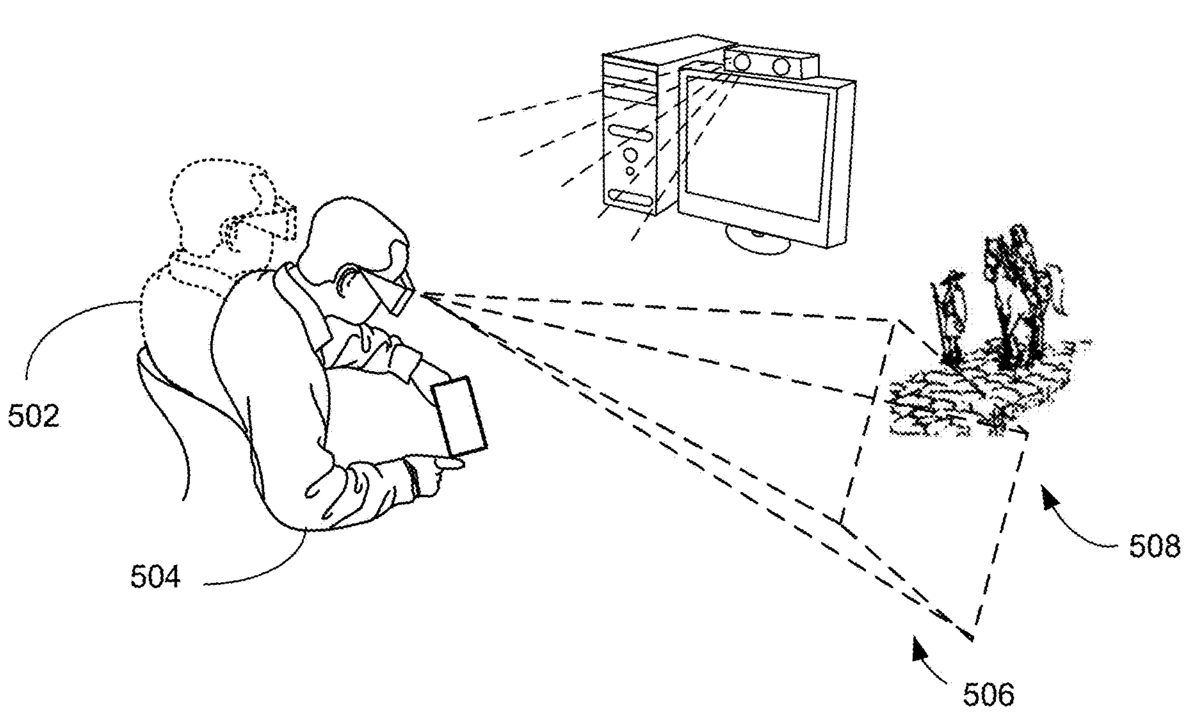

5. FIG. 5 is a diagram of a virtual reality system in accordance with aspects of disclosed implementations.

FIG. 5 is diagram of virtual reality system 400 showing a user's 502 previous posture in ghost lines and a user's bad posture. The sensor 410 has detected user's bad posture and the computing device 408 has determined an altered field of view 506 at step 312 of FIG. 3 to include a new scene 508 from the virtual world 424. In one example, the computing device 408 alters the field of view in response to the detecting of sensor 410. Virtual reality system 400 can render at step 314 of FIG. 3 and display at step 316 of FIG. 3 the new scene 508 in the altered field of view 506. In one example, the altered field of view 506 includes changing the field of view 420 to correspond with the posture of the user. The altered field of view 506 and the new scene 508 can be determined by virtual reality system 400 to be consistent with the location and scene that would have been viewed if the user's bad posture was controlling the location of the field of view, for example. This is illustrated in FIG. 5, where the altered field of view 506 is made consistent with the location and attitude of the user's bad posture. Changing the location of the altered field of view 506 and the new scene 508 to make them consistent with the user's bad posture can serve as a visual cue to the user 504 to correct the bad posture in an unobtrusive and natural way without having to use text or voice messages to alert the user that bad posture has been detected.

Interrupting the virtual reality experience by alerting the user 504 that bad posture had been detected through sound or text alerts can be regarded as an obtrusive and unwelcome interruption that can diminish the virtual reality experience. Alerting the user 504 by moving the field of view has the advantage of not requiring any additional actions on the user's part other than correcting the bad posture, for example clicking a controller to dismiss a dialog box in the field of view or on the display 412. By mimicking the effect that bad posture would have on a user's visual field in the real world, process 300 can elicit the correct physical response, which is to correct the bad posture, perhaps without even requiring conscious thought on the part of user 504 and therefore provides a natural and unobtrusive way to correct bad posture.

Returning to FIG. 3, at step 318 process 300 again detects the user's posture. At step 320 the detected posture is checked to see if it is bad. At this point in process 300, a user's bad posture has been detected at step 310 and the bad posture has been indicated to the user by the change in the field of view in steps 312, 314 and 316. At step 320 the process 300 is waiting for the user 504 to correct the detected bad posture. As long as bad posture is detected, process 300 loops back to step 318 to periodically detect user's posture. When bad posture is not detected, it can mean the user 504 has corrected the bad posture and process 300 has detected the corrected posture. This is illustrated in FIG. 6.

Figure 6:
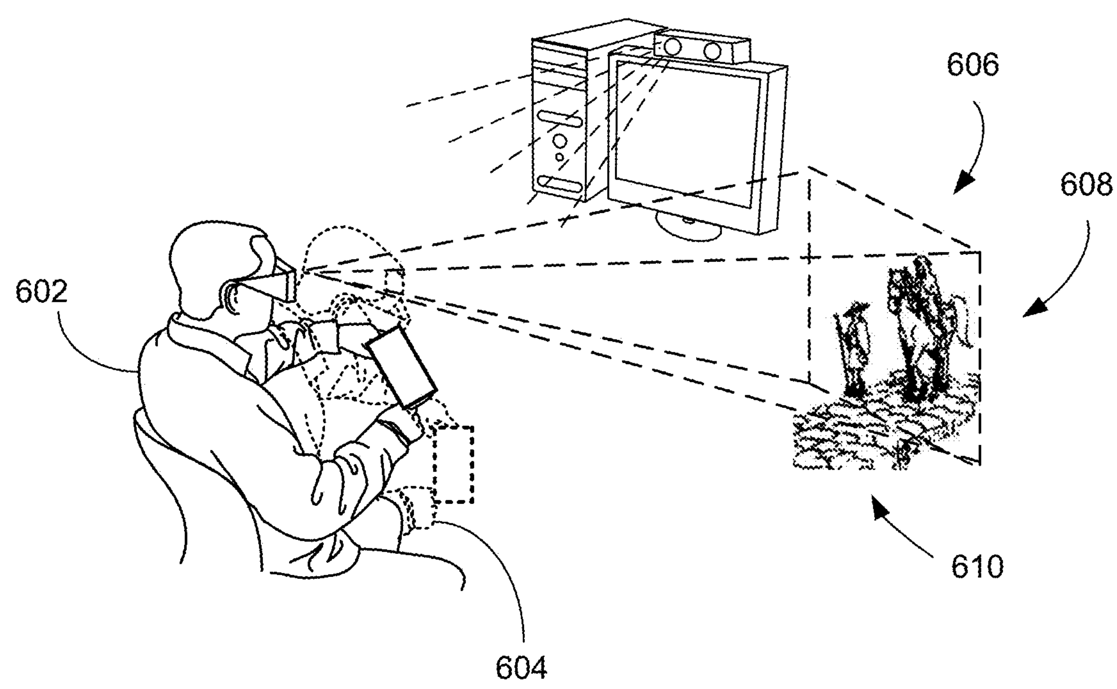
FIG. 6 is a diagram of a user at a virtual reality system in accordance with aspects of disclosed implementations.

FIG. 6 is a diagram of a virtual reality system 600 showing a user 602 having resumed good posture. Shown in ghost lines is the user 604 previously having bad posture. Virtual reality system 600 has detected the change from bad posture to good posture as described in steps 318 and 320 of FIG. 3. FIG. 6 shows a third field of view 606 positioned by the virtual reality system 600 to mimic the position the field of view 606 would assume based on the position of the user 602 having good posture. Positioning the field of view 606 to a third position permits the virtual reality system 600 to render and display the field of view 606 to display a scene 608 from the virtual world 610 similar to the scene 422 viewed by the user 602 prior to the virtual reality system detecting bad posture at step 310.

Returning to FIG. 3, at step 322, following a failure to detect bad posture at step 320, a third field of view can be determined. As discussed above in relation to FIG. 6, the position of the third field of view can be consistent with the user 602 exhibiting good posture again. At step 324 the field of view can be rendered for display and at step 326 the field of view can be displayed to the user 602. Following step 324 the user 602 can continue to experience the virtual world using the virtual reality system 600.

Aspects of disclosed implementations can also handle cases where, as described above, the virtual reality system is equipped with a VR headset having accelerometers that can detect the location and attitude of the VR headset and therefore the position of the user's head. A virtual reality system so equipped can use the location and attitude information from the VR headset to implement "looking around." In a virtual reality system so equipped, a user's location in the virtual world can be determined by the user by inputting commands via a handheld controller or a keyboard and mouse, for example. Once the location of a user in the virtual world is established, the user can "look around" the virtual world by moving their head. The VR headset can detect the head movements using accelerometers and move the field of view to mimic the head motions performed by the user and thereby change the virtual world scenes rendered and displayed on the VR headset.

Since the VR headset tracks the user's head motion (e.g., obtaining motion data or a motion signal) in this example, if a user exhibits bad posture that causes the field of view to move, the user will be alerted to the change in posture immediately since the field of view will change. Aspects of disclosed implementations can detect bad postures wherein the user has kept the field of view on a desired portion of the virtual world despite assuming a bad posture. An example of this might be a user "slumping" in a chair but keeping their head raised to keep looking at the same point in the virtual world despite slumping. This bad posture would not be immediately apparent to the user since the field of view has not changed.

Aspects of disclosed implementations can detect bad posture in the same manner as discussed above, using one or more video cameras with machine vision software, using one or more three-dimensional sensors with appropriate software or using one or more accelerometers to detect bad posture. Once the bad posture is detected, aspects can prompt the user to correct the problem by momentarily ignoring the input from accelerometers in the VR headset that determine the location and attitude of the field of view. The virtual reality system can move the field of view in a similar fashion as described above to approximate a field of view consistent with bad posture, even though the user may not be looking in that direction. Presenting the user with a moved field of view, even if it does not correspond to the actual direction of the user visual field, can elicit the same response as shown above: the user will stop the bad posture and assume good posture to correct the location of the field of view.

As the user assumes good posture, the virtual reality system can return control of the field of view to the accelerometers in the VR headset to permit the user to again control the field of view by head motions (e.g., obtaining motion data or a motion signal). This will have the same effect as described above, where bad posture can be detected and prompted for correction without any interruption, obtrusive measures, or actions on the part of the user beyond correcting the bad posture. In summary, aspects of disclosed implementations can detect and prompt for correction of bad postures by the user without requiring any actions on the part of the user beyond correcting the bad posture whether the virtual reality system is equipped to permit looking around by detecting head motion (e.g., obtaining motion data or a motion signal) or not.

The implementations of virtual reality systems described above illustrate some exemplary data processing techniques. However, data processing as those terms are used in the claims could mean creating, destroying, altering, computing, calculating, determining, selecting, storing, retrieving, or any other processing or change of data.

The words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same implementation unless described as such.

The implementations of computing devices such as the computing device 12, the computing device 14, the virtual reality computing device 200, the computing device 408, and the algorithms, methods, instructions, and such stored thereon and/or executed thereby can be realized in hardware, software, or any combination thereof. The hardware can include, for example, computers, intellectual property (IP) cores, ASICs, programmable logic arrays, optical processors, programmable logic controllers, microcode, microcontrollers, servers, microprocessors, digital signal processors or any other suitable circuit. In the claims, the term "processor" encompasses any of the foregoing hardware, either singly or in combination. The terms "signal" and "data" are used interchangeably. Further, portions of computing devices such as the computing device 12, the computing device 14, the virtual reality computing device 200, and the computing device 408 do not necessarily have to be implemented in the same manner.

Further, in one implementation, for example, computing devices such as the computing device 12, the computing device 14, the virtual reality computing device 200, and the computing device 408 can be implemented using a general-purpose computer/processor with a computer program that, when executed, carries out any of the respective methods, algorithms and/or instructions described herein. In addition, or alternatively, for example, a special purpose computer/processor can be utilized which can contain specialized hardware for carrying out any of the methods, algorithms, or instructions described herein.

Computing devices such as the computing device 12, the computing device 14, the virtual reality computing device 200, and the computing device 408, for example, be implemented on computers in a virtual reality system. Alternatively, the computing device 12 can be implemented on a server and the computing device 14, the virtual reality computing device 200, and the computing device 408 can be implemented on devices separate from the server, such as a cell phone or other hand-held communications device. In this instance, the computing device 12 can run the process 300 and transmit information to the computing device 14, the virtual reality computing device 200, and the computing device 408. Alternatively, the computing device 14, the virtual reality computing device 200, and the computing device 408 can run the process 300. Other suitable computing devices such as the computing devices such as the computing device 12, the computing device 14, the virtual reality computing device 200, and the computing device 408 are available. For example, computing devices such as the computing device 12, the computing device 14, the virtual reality computing device 200, and the computing device 408 can either be a generally stationary personal computer or a portable communications device.

Further, all or a portion of implementations of the present invention can take the form of a computer program product accessible from, for example, a computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or a semiconductor device. Other suitable mediums are also available.

The above-described implementations have been described in order to allow easy understanding of the present invention and do not limit the present invention. On the contrary, the invention is intended to cover various modifications and equivalent arrangements included within the scope of the appended claims, which scope is to be accorded the broadest interpretation so as to encompass all such modifications and equivalent structure as is permitted under the law.

What is claimed is:

1. A method, comprising:

obtaining a posture signal indicative of a posture of a user of a virtual reality display system; and outputting a field of view of a virtual reality scene to the virtual reality display system, wherein the field of view is a motion tracked field of view when the posture signal corresponds to good posture and the field of view is a moved field of view when the posture signal corresponds to bad posture.

2. The method of claim 1, further comprising:

obtaining a motion signal, wherein the motion tracked field of view is determined based on the motion signal.

3. The method of claim 2, wherein the moved field of view differs from the motion tracked field of view.

4. The method of claim 2, wherein the moved field of view ignores the motion signal.

5. The method of claim 2, wherein the motion signal represents a location and attitude of the virtual reality display system.

6. The method of claim 2, wherein the motion signal is obtained using one or more accelerometers.

7. The method of claim 1, wherein the posture signal is determined using at least one of a video camera or a three-dimensional sensor.

8. The method of claim 1, wherein the virtual reality display system is worn by the user on a head of the user.

9. A system, comprising:

a memory; and a processor configured to execute instructions stored in the memory to:

obtain a posture signal indicative of a posture of a user of a virtual reality display system, and output a field of view of a virtual reality scene to the virtual reality display system, wherein the field of view is a motion tracked field of view when the posture signal corresponds to good posture and the field of view is a moved field of view when the posture signal corresponds to bad posture.

10. The system of claim 9, wherein the processor is further configured to execute instructions stored in the memory to:

obtain a motion signal, wherein the motion tracked field of view is determined based on the motion signal.

11. The system of claim 10, wherein the moved field of view differs from the motion tracked field of view.

12. The system of claim 10, wherein the moved field of view ignores the motion signal.

13. The system of claim 10, wherein the motion signal represents a location and attitude of the virtual reality display system.

14. The system of claim 10, wherein the motion signal is obtained using one or more accelerometers, and the posture signal is determined using at least one of a video camera or a three-dimensional sensor.

15. A non-transitory computer-readable storage device including computer interpretable program instructions that, when executed by a computing device, cause the computing device to perform operations, the operations comprising:

obtaining a posture signal indicative of a posture of a user of a virtual reality display system; and outputting a field of view of a virtual reality scene to the virtual reality display system, wherein the field of view is a motion tracked field of view when the posture signal corresponds to good posture and the field of view is a moved field of view when the posture signal corresponds to bad posture.

16. The non-transitory computer-readable storage device of claim 15, the operations further comprising:

obtaining a motion signal, wherein the motion tracked field of view is determined based on the motion signal.

17. The non-transitory computer-readable storage device of claim 16, wherein the moved field of view differs from the motion tracked field of view.

18. The non-transitory computer-readable storage device of claim 16, wherein the moved field of view ignores the motion signal.

19. The non-transitory computer-readable storage device of claim 16, wherein the motion signal represents a location and attitude of the virtual reality display system.

20. The non-transitory computer-readable storage device of claim 16, wherein the motion signal is obtained using one or more accelerometers, and the posture signal is determined using at least one of a video camera or a three-dimensional sensor.

* * * * *